United States Patent
Steiner et al.

(12)

(10) Patent No.: US 6,232,501 B1
(45) Date of Patent: May 15, 2001

(54) PROCESS FOR THE CIS-SELECTIVE CATALYTIC HYDROGENATION OF CYCLOHEXYLIDENAMINES

(75) Inventors: Heinz Steiner, Bubendorf; Markus Benz, Arlesheim; Hans-Peter Jalett, Dornach; Marc Thommen, Toffen, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/646,211

(22) PCT Filed: Mar. 16, 1999

(86) PCT No.: PCT/EP99/01696

§ 371 Date: Sep. 14, 2000

§ 102(e) Date: Sep. 14, 2000

(87) PCT Pub. No.: WO99/47486

PCT Pub. Date: Sep. 23, 1999

(30) Foreign Application Priority Data

Mar. 18, 1998 (CH) ........................................ 645/98

(51) Int. Cl.[7] ........................ C07C 211/42; C07C 209/28
(52) U.S. Cl. ........................ 564/308; 564/397; 564/416; 564/417; 564/462
(58) Field of Search .................................. 564/308, 397, 564/416, 417, 462

(56) References Cited

U.S. PATENT DOCUMENTS

| 4,536,518 | | 8/1985 | Welch, Jr. et al. ................ 564/647 |
| 5,290,806 | * | 3/1994 | Zipperer et al. . |
| 5,708,026 | * | 1/1998 | Crossley et al. . |
| 6,046,360 | * | 4/2000 | Reuschling et al. . |

FOREIGN PATENT DOCUMENTS

| 93/01161 | 1/1993 | (WO) . |
| 98/270050 | 6/1998 | (WO) . |

OTHER PUBLICATIONS

R. Sarges, J. Org. Chem. vol. 40, No. 9, (1975), pp. 1216 "Synthesis of Phenyl—Substituted 1—Aminoletralines".

M. Lauten, J. Org. Chem. vol. 62, (1997) pp. 5246 "General Strategy Toward the Tetrahydronaphtalene Skeleton. An Expedient Total Synthesis of Sertraline".

R.B.C. Pillai, Journal of Molecular Catalysis, vol. 84, (1993), pp. 125 "Synthesis of secondary amino by reductive alkylation using copper chromite catalyst: steric effect of carbonyl compound".

* cited by examiner

*Primary Examiner*—Johann Richter
*Assistant Examiner*—Sikarl A. Witherspoon
(74) *Attorney, Agent, or Firm*—Kevin T. Mansfield

(57) ABSTRACT

This invention relates to a process for the cis-selective preparation of cyclic amines of the sertraline type by reductive alkylation of cyclic immines or of their precursors and for the catalytic hydrogenation in the presence of copper-containing catalysts.

5 Claims, No Drawings

PROCESS FOR THE CIS-SELECTIVE CATALYTIC HYDROGENATION OF CYCLOHEXYLIDENAMINES

The present invention relates to a novel, inventive process for the cis-selective catalytic hydrogenation of cyclohexylidenamines and their precursors.

Cyclohexylamines can be used, inter alia, as antioxidants and as pharmaceutical active substances. An important cyclohexylamine is sertraline:

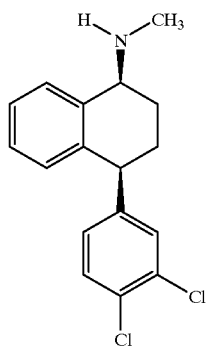

Sertraline: (1S,4S)-4-(3,4dichlorophenyl)-1,2,3,4-tetrahydro-N-methyl-1-napthylamine, see *Merck Index Twelfth Edition* 1996, No. 8612, is known as antidepressant. The preparation of this compound is described in U.S. Pat. No. 4,536,518. The hydrochloride is commercially available, inter alia under the registered trademarks Lustral® and Zoloft®. The cyclohexylamines of the type:

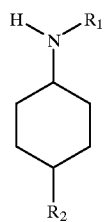

($R_2 \ne H$) exist in at least two isomeric forms:

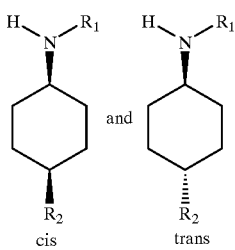

In another, non-symmetrical substitution at the cyclohexyl ring, the carbon atoms are chiral in 1- and 4-position. According to the R,S-nomenclature by Cahn, Ingold and Prelog, sertaline has the 1S-, 4S-configuration.

Cyclohexylamine is obtained, for example, by the following method: Reacting the ketone

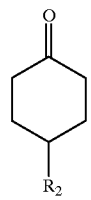

with a primary amine, e.g. methylamine, results, with elimination of water, in a cyclohexylidenamine:

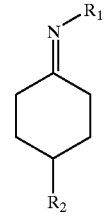

The resultant imine is then catalytically hydrogenated to the amine. These reactions proceed without, or only with minor, stereoselectivity. In the case of sertraline, four enantiomers are obtained.

This invention has for its object to prepare cyclohexylamines having as high as possible a cis-isomer proportion.

To achieve this object, the above-mentioned U.S. Pat. No. 4,536,518 proposes to hydrogenate an imine of formula:

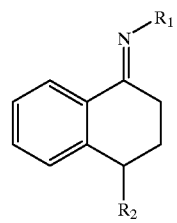

$R_2$ = 3,4-dichlorophenyl using palladium and carbon as substrates. This affords 70% of cis- and 30% of trans-racemate.

To further improve this yield, WO 93/01161 proposes to replace palladium and carbon as substrate by Raney nickel when hydrogenating the imine. This results in a cis/trans ratio of 8:1. Surprisingly, it has now been found that an even better cis/trans ratio is obtained if the imine is catalytically hydrogenated in the presence of a copper. The preparation of secondary amines from ketones and intermediate imines by hydrogenation in the presence of copper chromite catalysts is known from R. B. C. Pillai *J. Mol. Catalysis* 84 (1993), 125–129. However, it is surprising that, starting from cyclohexylidenamines, which are also obtainable as intermediates from ketones, the hydrogenation by means of a copper-containing catalyst proceeds diastereoselectively and affords a high cis-isomer proportion (>95%).

This invention relates to a process for the preparation of cis-compounds of formula:

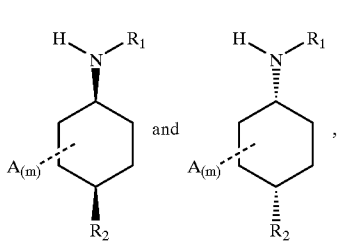
(I)

wherein $R_1$ and $R_2$ are each independently of the other hydrocarbon radicals and A is substituents, and m is an integer from 0 to 4 and defines the number of the substituents A, which process comprises a) hydrogenating a cyclohexylidenamine of formula:

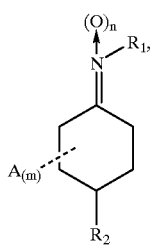
(II)

wherein n is 0 or 1 and $R_1$, $R_2$, A and m have the cited meanings, in the presence of a copper-containing catalyst; or b) reacting a ketone of formula:

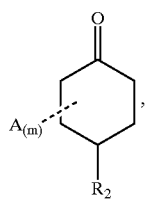
(III)

wherein $R_2$, A and m have the cited meanings, with a compound introducing the $R_1$—N→$(O)_n$ group, hydrogenating the imine or nitrone (II) which is obtainable as intermediate in the presence of a copper containing catalyst and isolating the cis-compound (I).

If in a compound (I) m is 0 and the cyclohexyl ring is unsubstituted, then the two structural formulae represent identical compounds:

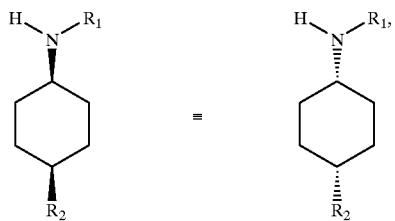
(I)

Of the two possibilities for representing the structural formula of the cis-compound (I) in the description of this invention, only the general formula:

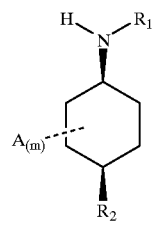
(I)

is used. If in a compound (I) m is 1 to 4 (m>0) and the cyclohexyl ring is unsymmetrically substituted, then a cis-enantiomer pair is selectively obtained during hydrogenation which can be separated into the optically pure antipodes by customary methods of racemate resolution, for example by crystallisation of the mandelic acid salt by the method of W. M. Welch et al in *J. Med. Chem.* 1984, 27, 1508–1515. The relationship between the two cis- and trans-enantiomer pairs and the 4 optically pure antipodes is illustrated by the following formula scheme of sertraline:

In the structural formulae of the starting materials (II) and (III), the unbroken bonding dashes to the substituent $R_2$ signify that in the case of $R_2 \neq H$ and of different substitution at the cyclohexyl ring, these starting materials can be used in the process in the form of racemic mixtures having identical or different antipode proportions or in the form of an optically pure antipode.

The process is distinguished by a high yield of the desired cis-compounds. In the case of the synthesis of sertraline, a ratio of the cis- to the trans-enantiomer pair is obtained which is higher than 95:5. In a particularly preferred embodiment of this invention, the even better ratio of higher than 99:1 is obtained. This high cis-compound yield obviates the separation of the cis- from the trans-enantiomer pair which is otherwise necessary when different substituents A (m>0) are present.

The definitions and denotations used within the scope of the description of this invention preferably have the following meanings:

A hydrocarbon radical $R_1$ or $R_2$ is preferably selected from the group consisting of $C_1$–$C_{20}$alkyl, $C_4$–$C_{12}$cycloalkyl, $C_2$–$C_{11}$heterocycloalkyl, carbocyclic $C_5$–$C_{16}$aryl, $C_2$–$C_{15}$heteroaryl, carbocyclic $C_7$–$C_{16}$aralkyl and $C_2$–$C_{15}$heteroarylalkyl and can in addition be substituted by suitable functional groups, for example by the functional groups or derivatised functional groups consisting of amino, $C_1$–$C_4$alkylamino, $C_1$–$C_4$dialkylamino, hydroxy, carboxy and halogen.

The cyclohexyl ring can be substituted by 1 to 4, preferably by 2, substituents from the group A containing the substituents $R_3$, $R_4$, $R_5$ and $R_6$. Suitable substituents are listed in the List of Radical Names, valid according to IUPAC Rules, and remain unchanged under the conditions of the catalytic hydrogenation reaction. Any of the substituents may be chosen. Suitable substituents A from the group $R_3$, $R_4$, $R_5$ and $R_6$ are selected, for example, from the group of the functional groups or derivatised functional groups consisting of amino, $C_1$–$C_4$alkylamino, $C_1$–$C_4$dialkylamino, hydroxy, carboxy and halogen, or are saturated or unsaturated aliphatic, cycloaliphatic or heterocycloaliphatic radicals, carbocyclic or heterocyclic aryl radicals, condensed carbocyclic, heterocyclic or carbocyclic-heterocyclic radicals, which can in turn be combined with any others of these radicals and which can be substituted by the cited functional groups or derivatised functional groups.

The cited substituents and radicals can furthermore be interrupted by one or more than one bivalent radical from the group consisting of —O—, —C(=O)—O—, —O—C(=O)—, —C(=O)—N($C_1$-$C_4$alkyl)—, —N($C_1$–$C_4$alkyl)—C(=O)—, —S(=O)$_2$—, —S(=O)$_2$—O—, —O—S(=O)$_2$—, —S(=O)$_2$—N($C_1$–$C_4$alkyl)—, —($C_1$–$C_4$alkyl)N—S(=O)$_2$—, —P(=O)——P(=O)—O—, —O—P(=O)— and —O—P(=O)—O—.

In a preferred embodiment of this invention, two substituents A from the group $R_3$, $R_4$, $R_5$ and $R_6$ are bivalent, bridge-like $C_2$–$C_6$alkylene, $C_4$–$C_8$alkyldiylidene or $C_4$–$C_8$alkenyldiylidene groups, preferably butanediylidene, more preferably 2-butenediylidene, which is bound with the cyclohexyl ring to two adjacent carbon atoms and which forms together with these carbon atoms a phenyl ring which can be substituted by the cited functional groups or substituents.

Suitable substituents A from the group $R_3$, $R_4$, $R_5$ and $R_6$ are also substituents from the group $C_1$–$C_{20}$alkyl, $C_4$–$C_{12}$cycloalkyl, $C_7$–$C_{12}$bicycloalkyl, $C_2$–$C_{11}$heterocycloalkyl, carbocyclic $C_6$–$C_{16}$aryl, $C_2$–$C_{15}$heteroaryl, carbocyclic $C_7$–$C_{16}$aralkyl and $C_2$–$C_{15}$heteroarylalkyl, which can in turn be substituted by the cited functional groups and interrupted by bivalent radicals.

$C_1$–$C_{20}$Alkyl is, for example, methyl, ethyl, n-, or iso-propyl or n-, sec- or tert-butyl and straight-chain or branched pentyl, hexyl, heptyl, octyl, isooctyl, nonyl, tert-nonyl, decyl, undecyl or dodecyl.

$C_4$–$C_{12}$Cycloalkyl is, for example, cyclopropyl, dimethylcyclopropyl, cyclobutyl, cyclopentyl or cyclohexyl.

$C_7$–$C_{12}$Bicycloalkyl is, for example, bornyl or norbornyl.

$C_2$–$C_{11}$Heterocycloalkyl preferably contains 4 or 5 carbon atoms and one or two heteroatoms from the group O, S and N. Examples are the substituents derived from oxirane, azirine, 1,2-oxathiolane, pyrazoline, pyrrolidine, piperidine, piperazine, morpholine, tetrahydrofuran or tetrahydrothiophene.

Carbocyclic $C_6$–$C_{16}$aryl is, for example, mono-, bi- or tricyclic, typically phenyl, naphthyl, indenyl, azulenyl or anthryl.

$C_7$–$C_{15}$Heteroaryl is preferably monocyclic or is condensed with a further heterocycle or with an aryl radical, for example phenyl, and preferably contains one or two, in the case of nitrogen up to four, heteroatoms from the group O, S and N. Suitable substituents are derived from furan, thiophene, pyrrole, pyridine, bipyridine, picoline, γ-pyran, γ-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, isoquinoline, acridine, chromene, phenazine, phenoxazine, phenothiazine, triazine, thianthrene, purine or tetrazole.

Carbocyclic $C_7$–$C_{16}$aralkyl preferably contains 7 to 12 carbon atoms, e.g. benzyl, 1- or 2-phenethyl or cinnamyl.

$C_2$–$C_{15}$Heteroarylalkyl preferably consists of the cited heterocycles, which substitute e.g. $C_1$–$C_4$alkyl radicals, depending on the length of the carbon chain where possible terminally, or else also in adjacent position (1-position) or in α-position (2-position).

In a preferred embodiment of this invention, a cis-enantiomer pair of the compound of formulae:

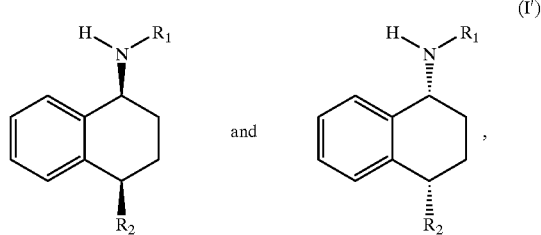

is prepared, wherein $R_1$ is $C_1$–$C_4$alkyl and $R_2$ is aryl.

According to process variant a) a cyclohexylidenamine, or the imine or nitrone (II), preferably the imine or nitrone of formula:

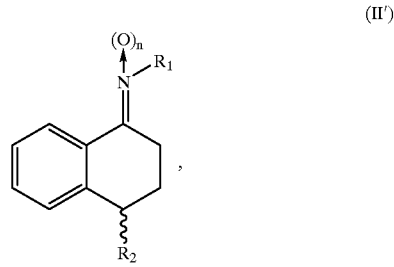

wherein $R_1$ and $R_2$ have the cited meanings, which imine or ketone may be in syn- or anti-form, is hydrogenated in the presence of a copper-containing catalyst According to process variant b) a ketone(III), preferably a ketone of formula

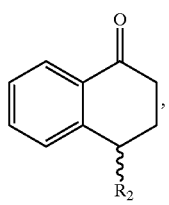

(III')

wherein $R_2$ has the cited meanings, is reacted with a compound introducing the $R_1$—N→(O)$_n$ group, in particular with a primary amine, preferably methylamine, or with a $R_1$-substituted hydroxylamine, Preferably N-methylhydroxylamine, and the imine (II) which is obtainable as intermediate is hydrogenated in situ in the presence of a copper-containing catalyst. It is also possible to replace the racemic compound (II') or (III') with an optically pure compound (II') or (III') and to react it to a cis-compound (I').

This invention preferably relates to a process for the preparation of the cis-compound (I'), wherein $R_1$ is methyl and $R_2$ is 3,4-dichlorophenyl, which process comprises a) hydrogenating an imine or nitrone (II'), wherein $R_1$ is methyl and $R_2$ is 3,4-dichlorophenyl, in the presence of a copper-containing catalyst, or b) reacting a ketone (III'), wherein $R_2$ is 3,4-dichlorophenyl, with methylamine or N-methyl-hydroxylamine, hydrogenating the imine or nitrone (II) which is obtainable as intermediate in the presence of a copper-containing catalyst and isolating the cis-compound (I').

Suitable catalysts for the hydrogenation reaction according to variants a) and b) are copper-containing catalysts, for example copper skeleton, copper substrate, copper chromite, copper zinc oxide, copper boride or copper urushibara catalysts.

In a preferred embodiment of this process, other elements are present in the catalyst besides copper. Examples thereof are aluminium, chromium, zinc, barium, manganese, zirconium, vanadium, molybdenum, titanium, tantalum, niobium, tungsten, nickel, cobalt, bismuth, tin, antimonium, hafnium, rhenium, iron, cadmium, lead or germanium and mixtures thereof. The amount in which the element is added can vary within wide limits and may be from 10 ppm to 200% in relation to the amount of copper used. Particularly suitable elements are aluminium, zinc, chromium, barium and manganese. The elements can be, for example, in the form of oxides or salts, such as chromates.

Raney copper is an example of a suitable copper skeleton catalyst

Examples of substrates are carbon, aluminium oxide, silicium dioxide, $Cr_2O_3$, zirconium dioxide, zinc oxide, calcium oxide, magnesium oxide, barium sulfate, calcium carbonate or aluminium phosphate. The copper can be bound on the substrate in an amount of about 1.0–20.0% by weight.

A suitable copper chromite catalyst is represented by the empirical formula $CuO.CuCr_2O_4$. $CuCr_2O_4$ is known, see C.A.R.N. 12018-10-9 and Gmelins Handbuch der Anorganischen Chemie, $8^{th}$ ed., Vol. Kupfer, part B, instalment 3, system number 60, page 60. A common name is also copper(II)chromate(III). Copper chromite catalysts having changing proportions of CuO and $CuCr_2O_4$, Raney copper catalysts and copper-zinc-aluminium-oxide catalysts are commercially available in pure form or in a form doped with the cited elements.

In a preferred embodiment of the process, the copper-containing catalysts used are copper chromite catalysts or catalysts containing copper, zinc and aluminium in the form of oxides.

The cited catalysts are present in the reaction mixture in an amount of about 0.1 to 100% by weight, preferably of 1–20% by weight, based on the amount of educt used.

The copper-containing catalysts can be used in different ways in the process:

in the form of ready-to-use catalysts;
in the form of prehydrogenated catalysts, or
in the form of catalysts prepared in situ from suitable precursors, such as copper salts or oxides, and from other compounds.

For the prehydrogenation it is possible to treat e.g. a suspension of the catalyst in a suitable solvent under 5 to 150 bar hydrogen at 80–250° C. for half an hour to 5 hours, or hydrogen is introduced under normal pressure up to 50 bar at 100 to 500° C. over the dry catalyst.

In preferred embodiment of the process, the catalyst used is activated by hydrogenation in the solvent which is used for hydrogenating the imine or nitrone ("prehydrogenation"). The catalyst can be separated after the hydrogenation e.g. by filtration if the process is carried out batchwise.

Imines (II) can be prepared by reacting ketones (II) with a compound introducing the $R_1$—N group, in particular with a primary amine, preferably methylamine. The preparation of imines (II) is carried out in analogy to the method which is described in U.S. Pat. No. 4,536,518.

Nitrones (II) can be prepared by reacting ketones (II) with a compound introducing the $R_1$—N→O group, for example $R_1$-substituted hydroxylamine, preferably N-methylhydroxylamine. The preparation of nitrones (II) is carried out in analogy to the method described in WO 98/27050.

Hydrogenation is carried out in the presence of an organic solvent. It is preferred to use non-polar or polar aprotic solvents or mixtures thereof.

Examples of suitable non-polar solvents are hydrocarbons, for example aliphatic hydrocarbons, such as hexane, heptane or petroleum ether, cycloaliphatic hydrocarbons, such as cyclohexane or methylcyclohexane, aromatic hydrocarbons, such as benzene, toluene or xylene.

Examples of suitable polar aprotic solvents are ethers, such as aliphatic ethers, e.g. 1,2-diethoxyethane or tert-butylmethyl ether, cyclic ethers, e.g. tetrahydrofuran or dioxan, amides, e.g. dimethylformamide or N-methylpyrrolidone. Ethers are particularly suitable, especially tetrahydrofuran.

In accordance with variant b) acid assistants are added where required, for example organic mono- or polyvalent acids containing more than two carbon atoms, for example acetic acid, propionic acid or malonic acid, mineral acids such as sulfuric acid, so-called Lewis acids, such as boron trifluoride, or so-called solid acids, such as zeolites or Nafion® and/or dehydrating agent, such as sodium sulfate.

In accordance with variant b) an excess of up to 50 mol of the amine used is added, for example methylamine in the form of methylamine gas or as a solution, e.g. in ethanol.

The process can be carried out in both variants preferably in the liquid phase batchwise or continuously, preferably with a catalyst suspension as liquid-phase hydrogenation or in a bubble column or with a formated catalyst in a trickle bed. The reaction can also be carried out in the gas phase with a powdered catalyst in a fluidised bed or with a formulated catalyst in a fixed bed.

The hydrogenation can be carried out in a wide range of temperatures. Temperatures in the range from 60° to about 250° C., preferably from 90° to 150° C., have been found to be advantageous.

The hydrogen pressure can vary within a wide range during hydrogenation, for example from 1–100, preferably from 5–50, more preferably from 10–20 bar. Which hydrogen pressure is used depends essentially on the hydrogenation plant available. At higher temperatures of about 100° C., molecular hydrogen can also be replaced by a hydrogen-donor, such as isopropanol.

The reaction time can vary within wide limits. It depends on the catalyst used, on the hydrogen pressure, on the reaction temperature and on the plant used and can be, for example, from half an hour to 24 hours. Advantageous reaction times are those from about half an hour to 2 hours.

The isolation of the reaction products is carried out by known methods and is illustrated in the Examples. After separation of the catalyst and removal of the solvent, the conventional separation processes may follow, for example preparative thin-layer chromatography, preparative HPLC, preparative gas chromatography etc.. The cis-racemate obtained starting from racemic cyclohexylidenamine can be separated into the optically pure antipodes without any further purification using the known processes for enantiomer separation, for example by means of preparative chromatography on chiral substrates (HPLC) or by precipitation or crystallisation using optically pure precipitants, for example D -(-) or L -(–)-mandelic acid or (+) or (–)-10-camphorsulfonic acid. Starting from enantiomer-pure 4-substituted cyclohexylideneamine, the enantiomer-pure 4-substituted cyclohexylamine is obtained directly by the hydrogenation process of this invention.

This invention also relates to the use of copper-containing catalysts for the diastereoselective hydrogenation of cyclohexylidenamines. In this case it is preferred to use copper chromite catalysts or CuZnAl-oxide catalysts for the diastereoselective hydrogenation of cyclohexylidenamines.

The following Examples illustrate the invention:

EXAMPLE 1
(Hydrogenation of the Imine)

0.1 g of barium-doped copper chromite catalyst (commercial product of Südchemie, Girdler G 13, comprising 29% of Cu, 26% of Cr and 13.6% of Ba) and 40 ml of THF are placed in a 100 ml autoclave (stainless steel 316SS). The catalyst suspension is prehydrogenated for 1 hour at 12 bar initial pressure $H_2$ at 130° C. The suspension is then cooled and 0.5 g of 4-(3,4-dichlorophenyl)-1-methylimino-1,2,3,4-tetrahydronaphthalene is added. Subsequently, hydrogenation is carried out for 18 hours at 100° C. and 12 bar initial pressure $H_2$ (maximum pressure: 15 bar). The catalyst is removed by filtration and the product is concentrated by evaporation under vacuum and dried under high vacuum. According to $^1$H-NMR spectrum, the cis/trans ratio of the resulting 4-(3,4-dichlorophenyl)-1,2,3,4-tetrahydro-N-methyl-1-naphthylamine is >95:5. The crude product is purified via FLASH chromatography over silica gel at a solvent gradient of $CH_2Cl_2$ to $CH_2Cl_2$/MeOH (9:1). This gives 83% of the theoretical yield of pure cis-racemate.

EXAMPLE 2
(Reductive Alkylation)

1.0 g of 4-(3,4-dichlorophenyl)-1-oxo-1,2,3,4-tetrahydronaphthalene and 0.2 g of barium-doped copper chromite catalyst (see Example 1) are placed in 40 ml of THF in a 100 ml autoclave (stainless steel 316SS). Subsequently, 2.25 ml of methylamine solution in ethanol (14.2% G/V) are added by means of a syringe. 120 bar of hydrogen are then forced in and hydrogenation is carried out for 16 hours at 110° C. and for 18 hours at 130° C. The catalyst is removed by filtration and the product is concentrated by evaporation under vacuum and dried under high vacuum. According to $^1$H-NMR spectrum, the cis/trans ratio of the resultant 4-(3,4-dichlorophenyl)-1,2,3,4-tetrahydro-N-methyl-1-napthylamine is >9:1. The crude product is purified via FLASH chromatography over silica gel at a solvent gradient of $CH_2Cl_2$ to $CH_2Cl_2$/MeOH (9:1). This gives 50% of the theoretical yield of pure cis-racemate.

EXAMPLE 3
(Hydrogenation of the Imine)

0.4 g of catalyst (commercial product of Engelhard, Cu-0890 P, comprising 35% of CuO, 42% of ZnO and 21% of $Al_2O_3$) and 80 ml of THF are placed in a 300 ml autoclave (stainless steel 316SS). The catalyst suspension is prehydrogenated for 2 hours at 10 bar initial pressure $H_2$ at 150° C. The suspension is then cooled and 2 g of 4-(3,4-dichlorophenyl)-1-methylimino-1,2,3,4-tetrahydronaphthalene are added. Subsequently, hydrogenation is carried out for 30 minutes at 100° C. and at 10 bar initial pressure $H_2$ (maximum pressure: 15 bar). The catalyst is removed by filtration (over Hyflo®) and 0.5 ml of the solution are concentrated by evaporation under vacuum. The sample is taken up in isopropanol and the cis/trans ratio of the resultant 4-(3,4-dichlorophenyl)-1,2,3,4-tetrahydro-N-methyl-1-napthylamine is determined via HPLC: 97.3 to 2.7. 20 ml of a HCl-saturated THF solution are then added dropwise at 0° C. to the solution of crude product. The corresponding crystalline hydrochloride precipitates and is collected by filtration over a glass suction filter and dried under vacuum. This gives 85% of the theoretical yield of pure cis-racemate. The melting point is 292–2930° C. after recrystallisation from absolute methanol.

EXAMPLE 4
(Hydrogenation of the Imine, without Prehydrogenation of the Catalyst)

0.06 g of catalyst (commercial product of Engelhard Cu-0890 P, comprising 35% of CuO, 42% of ZnO and 21% of $Al_2O_3$), 30 ml of THF and 3 g of 4-(3,4-dichlorophenyl)-1-methyl-imino-1,2,3,4-tetrahydronaphthalene are placed in a 100 ml autoclave (stainless steel 316SS). Hydrogenation is then carried out for 1½ hours at 150° C. and at 10 bar initial pressure $H_2$ (maximum pressure: 15 bar). The catalyst is removed by filtration over Hyflo® and 0.1 ml of the solution is concentrated by evaporation under vacuum. The sample is taken up in isopropanol and the cis/trans ratio of the resultant 4-(3,4-dichlorophenyl)-1,2,3,4-tetrahydro-N-methyl-1-napthylamine is determined via HPLC: 99.0:1.0. Subsequently, 1.5 g of D-(–)-mandelic acid are added to the solution of crude product and the solvent is stripped off, with heating, in a rotary evaporator. After drying for 12 hours under high vacuum, 100 ml of ethanol are added and the corresponding crystalline mandelate is dissolved under reflux conditions. After heating for 20 minutes the solution is cooled and stored overnight at room temperature. The colourless crystals are filtered over a glass suction filter and the mother liquor is concentrated to half its volume and, after brief heating, cooled to the second crystallisation. This gives a further product fraction. The total yield is 82% of theory. The melting points are 191° C. and 190° C. for the first and second fraction, respectively.

EXAMPLE 5

(Hydrogenation of the Nitrone, with Prehydrogenation of the Catalyst)

428 mg of catalyst (commercial product of Engelhard Cu-0890 P) and 35 ml of THF are placed in a 100 ml autoclave (stainless steel 316SS). The catalyst suspension is prehydrogenated for 2 hours at 12 bar initial pressure $H_2$ at 150° C. The suspension is cooled and then 3.01 g (9.4 mmol) of 4-(3,4-dichlorophenyl)-1-methyloxidoimino-1,2,3,4-tetrahydronaphthalene are added. Hydrogenation is then carried out for 90 minutes at 130° C. and at 12 bar initial pressure $H_2$. The catalyst is removed by filtration and the product is concentrated by evaporation under vacuum and dried under high vacuum. The cis/trans ratio of the resultant 4-(3,4-dichlorophenyl)-1,2,3,4-tetrahydro-N-methyl-1-naphthylamine according to HPLC is >98.5 in favour of the cis-compound.

EXAMPLE 6

In analogy to Example 3, 4-(3,4-dichlorophenyl)-1-methylimino-1,2,3,4-tetrahydronaphthalene is hydrogenated using the catalysts X 572P (Engelhard, CuO, $CaSiO_x$,C), X 540 P (Engelhard CuO, $AlO_x$, $MnO_2$) and Cu1890P (Engelhard $CuCrO_x$, 42% Cu, 31% Cr). The cis/trans ratio according to HPLC is 98.0 (X572P), 98.3 (X540P) and 99.2 (Cu1890P) in favour of the cis-compound.

What is claimed is:

1. A process for the preparation of a compound of formula

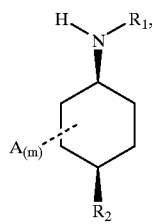

(I)

wherein $R_1$ and $R_2$ are each independently of the other hydrocarbon radicals and A is substituents, and m is an integer from 0 to 4 and defines the number of the substituents A, which process comprises a) hydrogenating a cyclohexylidenamine of formula:

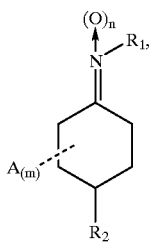

(II)

wherein n is 0 or 1 and $R_1$, $R_2$, A and m have the cited meanings, in the presence of a copper-containing catalyst; or b) reacting a ketone of formula:

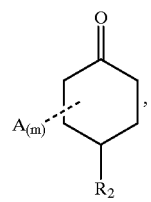

(III)

wherein $R_2$, A and m have the cited meanings, with a compound introducing the $R_1$—N→$(O)_n$ group, hydrogenating the imine or nitrone (II) which is obtainable as intermediate in the presence of a copper-containing catalyst and isolating the cis-compound (I).

2. A process for the preparation of a compound of formula I, wherein the hydrocarbon radicals $R_1$ or $R_2$ are selected from the group consisting of $C_1$—$C_{20}$alkyl, $C_4$—$C_{12}$cycloalkyl, $C_4$-$C_{12}$cycloalkenyl, $C_2$-$C_{11}$heterocycloalkyl, carbocyclic $C_6$–$C_6$aryl, $C_2$-$C_{15}$heteroaryl, carbocyclic $C_7$–$C_{16}$aralkyl and $C_2$-$C_{15}$heteroarylalkyl and are substituted by functional groups from the group consisting of amino, $C_1$–$C_4$alkylamino, $C_1$–$C_4$dialkylamino, hydroxy, carboxy and halogen, m is 2 and A is the substituents $R_3$ and $R_4$ which are each independently of one another or in combination saturated aliphatic, cycloaliphatic or heterocycloaliphatic radicals or carbocyclic, heterocyclic or carbocyclic-heterocyclic radicals which may be combined with any others of these radicals and which may be substituted by functional groups from the group consisting of amino, $C_1$–$C_4$alkylamino, $C_1$–$C_4$dialkylamino, hydroxy, carboxy and halogen, which process comprises a) carrying out the process variant a) with a corresponding substituted imine (II), wherein m is 2 and $R_1$, $R_2$, $R_3$ and $R_4$ have the cited meanings, or b) carrying out the process variant b) with a corresponding substituted ketone (II), wherein m is 2 and $R_3$ and $R_4$ has the cited meanings.

3. A process according to either claim 1 for the preparation of the cis-enantiomer pair of the compound of formula

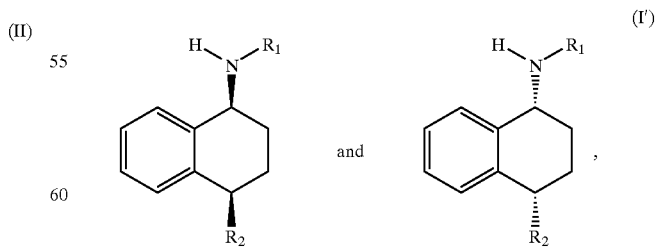

(I')

wherein $R_1$ is $C_1$–$C_4$alkyl and $R_2$ is aryl, which process comprises a) hydrogenating an imine or nitrone of formula

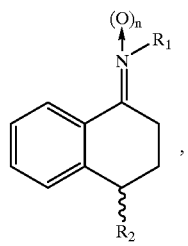
(II')

wherein $R_1$ is methyl and $R_2$ is 3,4-dichlorophenyl, in the presence of a copper-containing catalyst; or b) reacting a ketone of formula

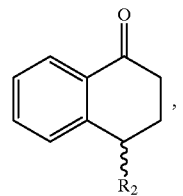
(III')

wherein $R_2$ has the cited meanings, with a compound introducing the $R_1$—N group, hydrogenating in situ the imine or nitrone (II) which is obtainable as intermediate in the presence of a copper-containing catalyst and isolating the compound (I').

4. A process according to claim 3 for the preparation of the cis-compound (I'), wherein $R_1$ is methyl and $R_2$ is 3,4-dichlorophenyl, which comprises a) hydrogenating an imine or nitrone (III), wherein $R_1$ is methyl and $R_2$ is 3,4-dichlorophenyl, in the presence of a copper-containing catalyst, or b) reacting a ketone (III'), wherein $R_2$ is 3,4-dichlorophenyl, with methylamine or N-methylhydroxylamine, hydrogenating the imine or nitrone (II) which is obtainable as intermediate in the presence of a copper-containing catalyst and isolating the cis-compound (I').

5. A process according to claim 1, which comprises preparing the compound (I) by hydrogenation in the presence of a copper chromite or CuZnAl-oxide catalyst.

* * * * *